United States Patent [19]

Heinemann et al.

[11] Patent Number: 4,537,975
[45] Date of Patent: Aug. 27, 1985

[54] 1-PHENYLINDAZOL-3-ONE COMPOUNDS

[75] Inventors: Henning Heinemann, Hanover, Fed. Rep. of Germany; Daniel Jasserand, Paris, France; Wolfgang Milkowski, Burgdorf, Fed. Rep. of Germany; Dimitri Yavordios, Chatillon-sur-Chalaronne, France; Horst Zeugner, Hanover, Fed. Rep. of Germany

[73] Assignee: Kali-Chemie Pharma GmbH, Hanover, Fed. Rep. of Germany

[21] Appl. No.: 564,398

[22] Filed: Dec. 22, 1983

Related U.S. Application Data

[62] Division of Ser. No. 409,632, Aug. 19, 1982, Pat. No. 4,448,777.

[30] Foreign Application Priority Data

Aug. 20, 1981 [DE] Fed. Rep. of Germany ....... 3132916

[51] Int. Cl.$^3$ ................ C07D 231/56; C07D 403/06; A61K 31/495
[52] U.S. Cl. ................................. 548/359; 544/364; 544/371
[58] Field of Search ............................... 548/372, 359

[56] References Cited

PUBLICATIONS

Baiocchi et al. (I), Chem. Abst. 72, 90367p, (1970).
Baiocchi et al. (II), Synthesis, No. 9, pp. 633–648, (1978).
Palazzo et al., J. Med. Chem, 9, pp. 38–41, (1966).

Primary Examiner—Richard A. Schwartz
Assistant Examiner—Kurt G. Briscoe
Attorney, Agent, or Firm—Schwartz, Jeffery, Schwaab, Mack, Blumenthal & Evans

[57] ABSTRACT

Compounds corresponding to the formula:

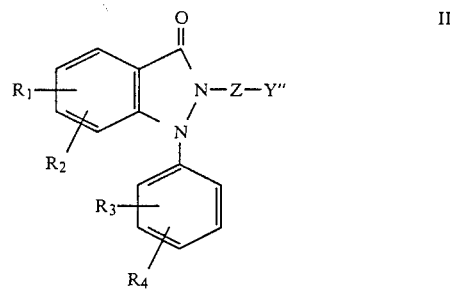

wherein $R_1$ and $R_3$ each represent hydrogen, halogen, lower alkyl, lower alkoxy or trifluoromethyl; $R_2$ and $R_4$ each represent hydrogen, halogen, lower alkyl or lower alkoxy; Z represents an alkylene radical with 2 to 6 carbon atoms and Y" is halogen, hydroxyl, lower alkanesulphonyl, benzenesulphonyl, or lower alkyl or halogen substituted benzenesulphonyl, and acid addition salts thereof, with the proviso the Y" is other than chlorine if $R_1$, $R_2$, $R_3$ and $R_4$ each are hydrogen and Z is ethylene or propylene. The claimed compounds are useful intermediates in the synthesis of 1-phenyl-2-[(4-substituted piperazinyl) alkyl]-1,2-dihydro-3H-indazol-3-ones which exhibit antiallergic activity.

6 Claims, No Drawings

1-PHENYLINDAZOL-3-ONE COMPOUNDS

This is a division of application Ser. No. 409,632 filed Aug. 19, 1982, now U.S. Pat. No. 4,448,777.

BACKGROUND OF THE INVENTION

This invention relates to novel 2-piperazinoalkyl-1-phenylindazol-3-one compounds and salts thereof, and to pharmaceutical compositions containing these compounds. The invention also relates to a method for preparing these compounds, as well as to intermediate products for use in the preparation of these compounds. The preparation of 1-phenyl-2-(3-chloropropyl)-1,2-dihydro-3H-indazol-3-one is known from a work on 1H-indazol-3-ols and 1,2-dihydro-3H-indazol-3-ones by L. Baiocchi et al. (Synthesis, 1978, 633-648).

SUMMARY OF THE INVENTION

It is an object of the present invention to provide new 1-phenylindazol-3-one compounds which are substituted in the 2-position and have valuable pharmacological properties, and to provide a method for their preparation.

It has now been found that the present novel 1-phenyl-indazol-3-one compounds have valuable pharmacological properties, in particular marked antiallergic properties, and in addition also cardiovascular and psychopharmacological properties, and have an advantageous action profile with a good therapeutic range and low toxicity. On the basis of these properties, the new compounds are suitable as medicaments for the treatment of allergic illnesses, such as, for example, asthma or hay fever of allergic origin.

According to one aspect of the present invention there is provided a 1-phenylindazol-3-one compound of the general formula I

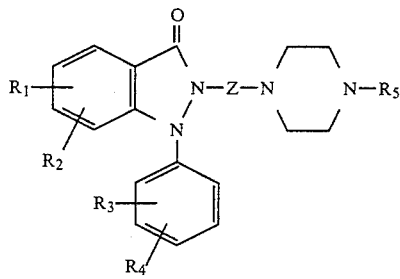

where $R_1$ is a hydrogen or halogen atom, or a lower alkyl, lower alkoxy, or trifluoromethyl radical, $R_2$ is a hydrogen or halogen atom, or a lower alkyl or lower alkoxy radical, $R_3$ is a hydrogen or halogen atom, or a lower alkyl, lower alkoxy or trifluoromethyl radical, $R_4$ is a hydrogen or halogen atom, or a lower alkyl or lower alkoxy radical, Z is an alkylene radical with 2 to 6 carbon atoms, and $R_5$ is an unsubstituted pyridyl radical or a pyridyl radical which is monosubstituted by a halogen atom or a lower alkyl or lower alkoxy radical, a thienyl radical or an unsubstituted or substituted phenyl radical a

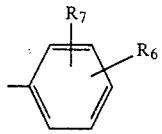

where $R_6$ is a hydrogen or halogen atom, or a lower alkyl, lower alkoxy, hydroxyl, trifluoromethyl or lower alkanoyloxy radical, and $R_7$ is a hydrogen or halogen atom, or a lower alkyl or lower alkoxy radical, or $R_6$ and $R_7$ are bonded to adjacent carbon atoms and together denote a methylenedioxy or ethylenedioxy radical; and acid addition salts thereof.

If the substituents $R_1$ to $R_4$ and the substituents in the radical $R_5$ in the compound of formula I contain a lower alkyl group, this can be straight-chain or branched and preferably contains 1 to 4 carbon atoms. Particularly suitable alkyl groups are thus methyl, ethyl, n-propyl, isopropyl, n-butyl and tert.-butyl, methyl, ethyl, n-propyl and isopropyl being preferred. Methyl or ethyl, in particular methyl, are the preferred alkyl radicals, especially in the case of disubstitution on the phenyl rings. Lower alkoxy substituents are preferably methoxy or ethoxy.

Suitable halogen substituents include fluorine, chlorine and bromine. If $R_1$ is a trifluoromethyl radical $R_2$ is preferably a hydrogen atom. In the case of halogen and/or alkyl, or and/or alkoxy substituents, monosubstitution or disubstitution is advantageous. Preferred positions for the substituents $R_1$ and $R_2$ are the 5- and 6-positions. If the phenyl radical a is substituted by a trifluoromethyl radical, monosubstitution is preferred. In the case of halogen and/or alkyl or and/or alkoxy substituents, monosubstitution or disubstitution is advantageous.

The radical Z is a straight or branched alkylene chain with 2 to 6 carbon atoms, alkylene chains with 2 to 4 carbon atoms being preferred.

If $R_5$ is a pyridyl group, this can be bonded to the remainder of the molecule in the 2-, 3- or 4-position, preferably in the 2-position. The pyridyl group can be unsubstituted or substituted by one of the abovementioned substituents, in particular a lower alkyl or alkoxy radical, preferably a methyl or methoxy radical.

If $R_5$ is a thienyl group, this can be bonded to the remainder of the molecule in the 2- or 3-position, preferably in the 2-position.

According to another aspect of the present invention there is provided a compound of the general formula II

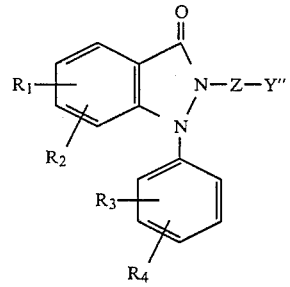

where $R_1$ is a hydrogen or halogen atom, or a lower alkyl, lower alkoxy, or trifluoromethyl radical, $R_2$ is a hydrogen or halogen atom, or a lower alkyl or lower alkoxy radical, $R_3$ is a hydrogen or halogen atom, or a lower alkyl, lower alkoxy or trifluoromethyl radical, $R_4$ is a hydrogen or halogen atom, or a lower alkyl or lower alkoxy radical, Z is an alkylene radical with 2 to 6 carbon atoms and Y" is a radical which can be split off by aminolysis or a hydroxyl radical; and acid addition salts thereof.

According to yet another aspect of the present invention there is provided a compound of the general formula III

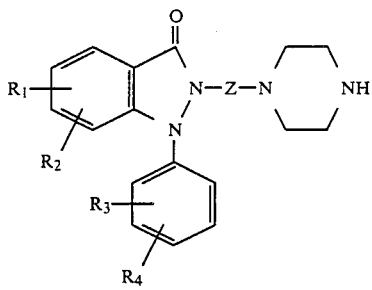

III where $R_1$ is a hydrogen or halogen atom, or a lower alkyl, lower alkoxy or trifluoromethyl radical, $R_2$ is a hydrogen or halogen atom, or a lower alkyl or lower alkoxy radical, $R_3$ is a hydrogen or halogen atom, or a lower alkyl, lower alkoxy or trifluoromethyl radical, $R_4$ is a hydrogen or halogen atom, or a lower alkyl or lower alkoxy radical and Z is an alkylene radical with 2 to 6 carbon atoms; and acid addition salts thereof.

According to a further aspect of the present invention, the new 1-phenylindazol-3-one compounds of formula I and acid addition salts thereof are obtained by a method wherein either (a) a compound of formula IIa

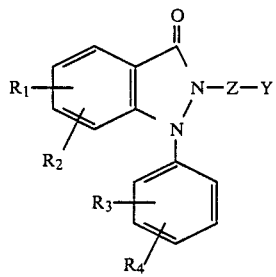

IIa where $R_1$, $R_2$, $R_3$, $R_4$ and Z have the meanings as defined above, and Y is a radical which can be split off by aminolysis, is reacted with a compound of formula V

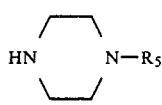

V where $R_5$ has the meaning defined above, or (b) for the preparation of a compound of formula Ia

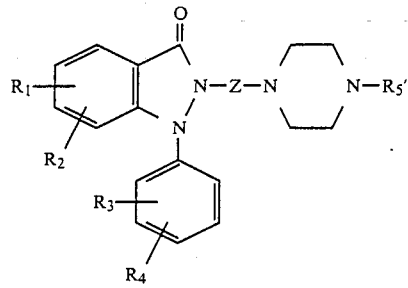

Ia where Z, $R_1$, $R_2$, $R_3$ and $R_4$ have the above defined meanings and $R_5'$ is a substituted phenyl group a'

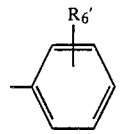

a' where $R_6'$ is a trifluoromethyl radical in the ortho- or para-position a compound of the formula III

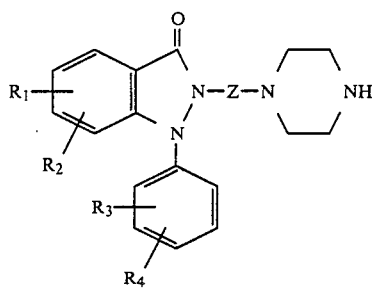

III where $R_1$, $R_2$, $R_3$, $R_4$ and Z have the above defined meanings, is reacted with a compound of the formula IV

IV where $R_6'$ has the above defined meaning and U is a halogen atom, and wherein, in the case where the compound of formula I is obtained in the form of the free compound it may be converted into its acid addition salt in the case where the compound of formula I is obtained from an acid addition salt the latter may be converted into the free compound.

DETAILED DESCRIPTION OF THE INVENTION

The reaction of the compound of formula IIa with a compound of formula V according to process variant (a) can be carried out by methods which are customary per se for the alkylation of amines.

The reaction is advantageously carried out at elevated temperature, for example at a temperature of from 50° to 150° C., in particular from 90° to 150° C., under basic conditions. Possible radicals, in compounds of the formula IIa, which can be split off by aminolysis are, in particular, halogens, such as chlorine, bromine or iodine, preferably chlorine or bromine, and also organic sulphonic acid radicals, in particular radicals of lower alkanesulphonic acids, such as, for example, methanesulphonic acid or ethanesulphonic acid, or of aromatic sulphonic acids, in particular benzenesulphonic acids or benzenesulphonic acids which are substituted by lower alkyl, for example toluenesulphonic acids, or benzenesulphonic acids which are substituted by halogen, such as, for example, bromobenzenesulphonic acids. The reaction is advantageously carried out in an organic solvent which is inert under the reaction conditions. Examples of suitable solvents include aromatic hydrocarbons, such as benzene, toluene and xylene, cyclic ethers, such as dioxane, dimethylformamide, 1,3-dimethyl-2-imidazolidinone, hexamethylphosphoric acid triamide, sulpholane, dimethylsulphoxide, tetramethylurea and lower alkanols, such as, for example, isopentanol. If desired, the reaction of the compound of formula IIa with the compound of formula V can, however, also take place in the melt without a solvent. The reaction can advantageously be carried out with the addition of an organic or inorganic base. However, it is also possible to use an excess of the compound of formula V and to utilise this as an internal base. Particularly suitable inorganic bases are alkali metal carbonates and bicarbonates, such as sodium carbonate, sodium bicarbonate and potassium carbonate. Suitable organic bases are tertiary organic amines, preferably tertiary lower alkylamines, such as triethylamine, n-tripropylamine, n-tributylamine and 1,4-dimethylpiperazine.

If either or both of the compounds of formula IIa and V contain free hydroxyl groups as substituents, these are advantageously provided with a protecting group in a manner which is known per se during the reaction. Suitable protecting group which can easily be split off again after the reaction are known from, for example, E. McOmie "Protective Groups in Organic Chemistry" Plenum Press (1971). For example, ethers, in particular tetrahydropyranyl ethers, are suitable for protecting a hydroxyl group. These protecting groups can easily be removed again in a known manner after the reaction.

The reaction of the compound of formula III with the compound of formula IV can likewise be carried out in a manner which is known per se under the conditions customary for the alkylation of amines, for example the conditions mentioned above for the reaction of a compound of formula IIa with a compound of formula V. The substituted halogenated phenyl compounds are sufficiently activated by the presence of a second order substituent to be capable of reacting with the piperazine derivative of formula III.

The compounds of formula I can be isolated from the reaction mixture, and purified, in a manner which is known per se. If the compound is obtained in the form of an acid addition salt, this salt can be converted into the free base in the customary manner, and, if desired, the base can be converted into a pharmacologically acceptable acid addition salt in known manner.

Examples of suitable pharmacologically acceptable acid addition salts of the compounds of formula I are their salts with hydrochloric acid, hydrobromic acid, sulphuric acid, phosphoric acid, methanesulphonic acid, ethanesulphonic acid, benzenesulphonic acid, p-toluenesulphonic acid, citric acid, acetic acid, lactic acid, succinic acid, maleic acid, fumaric acid, malic acid, tartaric acid, benzoic acid, phenylacetic acid and mandelic acid.

The compounds of formula I contain two or, if $R_5$ denotes an optionally substituted pyridyl radical, three basic centres and can thus form acid addition salts with one, two or three equivalents of an acid. Mono-acid salts are particularly suitable for the preparation of pharmaceutical compositions. Salt which contain several equivalents of acid can, if desired, be converted into mono-acid salts in a manner which is known per se, for example by conversion into the free base and subsequent reaction of the base with an equivalent amount of acid.

Compounds of formula I where Z is a branched alkylene radical are obtained in the form of their racemates in the synthesis. Both the racemic mixtures and also the optically active forms of these compounds fall within the protection of the present invention. The optically active compounds can be separated out of the racemic mixtures into their optically active antipodes in a manner which is known per se by reaction with suitable optically active acids, such as, for example, tartaric acid, O,O'-dibenzoyl-tartaric acid, mandelic acid or di-O-isopropylidene-2-oxo-L-gulonic acid, and subsequent fractional crystallisation of the salts obtained (see for example, Tetrahedron 33 (1977) pages 2725 to 2736).

With the exception of those compounds in which $R_1$ to $R_4$ are hydrogen atoms and the Z—Y" radical is a chloropropyl or chloroethyl radical, compounds of formula II have not yet been described in the literature and are novel valuable intermediate products for the preparation of pharmacologically active compounds, for example the compounds of formula I.

Compounds of formula II can be obtained by processes which are known per se, by reacting an alkali metal salt of a 1-phenyl-1,2-dihydro-3H-indazole-3-one compound of the general formula VI

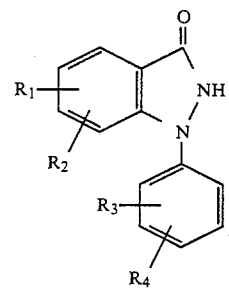

VI where $R_1$, $R_2$, $R_3$ and $R_4$ have the above defined meanings, with a compound of the formula VII

Y—Z—Y'  VII where Z and Y have the above defined meanings and Y' is a protected hydroxyl group or a radical Y which can be split off by aminolysis. Possible radicals Y which can be split off by aminolysis include, in particular, chlorine, bromine and iodine atoms and reactive acid radicals, for example the abovementioned organic sulphonic acid radicals. Y' is preferably a chlorine or bromine atom or a protected hydroxyl group. The conventional protecting groups, such as, for example, ethers, in particular tetrahydropyranyl ether, can be used to protect the hydroxyl group during the reaction. Suitable protecting groups for the hydroxyl group which can easily be removed again, when the reaction has ended, by processes which are known per se are known from, for example, E. McOmie "Protective Groups in Organic Chemistry", Plenum Press, London 1971, page 95 et seq.

The reaction is advantageously carried out in a solvent which is inert under the reaction conditions, at a temperature of from 0° C. up to the boiling point of the solvent, a temperature of from 0° C. to 100° C. being generally preferred. Examples of suitable solvents include lower alcohols, such as methanol, ethanol, isopropanol, butanol and tert.-butanol, and aromatic hydrocarbons, such as benzene and toluene, dimethylformamide, sulpholane, hexamethylphosphoric acid triamide, tetramethylurea and cyclic ethers, such as, for example, dioxane and tetrahydrofuran.

Suitable alkali metal salts of the 1-phenyl-1,2-dihydro-3H-indazol-3-one compounds include the lithium, sodium and potassium salts, preferably the sodium salts, and these can be obtained in situ by reacting a compound of formula VI with an alkali metal alcoholate or hydride. When the 1-phenyl-1,2-dihydro-3H-indazol-3-one compound of formula VI is alkylated with a compound of formula VII, a mixture of the desired N-alkylated product and the corresponding isomeric O-alkylated product is generally obtained. The N-alkylated product can be separated off from the mixture by chromoatography or crystallisation.

The O-alkylated by-product can be rearranged into the corresponding N-alkylated product simply by heating. The rearrangement temperature is advantageously from 60° to 200° C. If desired, the rearrangement can be carried out in the presence of an inert solvent, advantageously at the boiling point of the solvent. Examples of suitable solvents are lower alcohols with boiling points within the given range, for example methanol, butanol and isopentanol, and aromatic hydrocarbons, such as benzene, toluene and xylene. The mixture of N-alkylated product and corresponding isomeric O-alkylated product obtained during the alkylation can also be used directly for the rearrangement reaction under the influence of heat, without first being separated into its components.

When the reaction of the compound of formula VI with the compound of formula VII has ended, a protected hydroxyl group can, by processes which are known per se, be freed again by splitting off the protecting group and be reacted with a conventional halogenating agent, such as, for example, thionyl chloride, phosphorus oxychloride or phosphorus tribromide, in order to give a compound of formula IIa where Y is a halogen atom; alternatively, the freed hydroxyl group can be esterified by methods which are known per se. For example it can be reacted with a corresponding acid halide, to give a compound of formula IIa where Y is a reactive ester radical, in particular one of the above-mentioned sulphonic acid radicals.

Compounds of formula III have not yet been described in the literature, and are novel valuable intermediate products for the preparation of the pharmacologically active compounds, for example the compounds of formula I.

Compounds of formula III can be obtained by methods which are known per se, for example by reacting a compound of formula IIa with an excess of piperazine. The reaction can be carried out by methods which are customary per se for the alkylation of amines, for example under the conditions described above for the reaction of a compound of formula IIa with a compound of formula V.

A compound of formula III can also be obtained from a compound of formula VIII

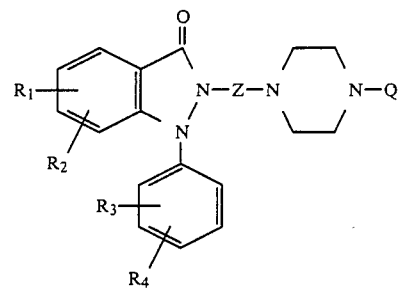

where $R_1$, $R_2$, $R_3$, $R_4$ and Z have the above defined meanings and Q is an amine-protecting group, by splitting off the amine-protecting group in a manner which is known per se. Suitable amine-protecting groups include the conventional protecting groups which are known per se for protection of an amine group, for example an acyl group which can be split off by hydrolysis or a benzyl group which can be split off by hydrogenolysis. Suitable protecting groups are known from, for example, E. McOmie "Protective Groups in Organic Chemistry"; Plenum Press, (1971) London page 44 et seq. The formyl group and lower carbalkoxy protective groups are particularly suitable. These groups can be split off by acid or alkaline hydrolysis in a manner which is known per se. Compounds of the formula VIII can be obtained in a manner which is known per se, for example by reacting a compound of formula IIa with a compound of formula IX

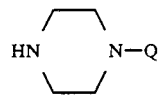

where Q has the above defined meaning. The reaction can be carried out by methods customary for the alkylation of amines, for example under the reaction conditions described above for the reaction of a compound of formula IIa with a compound of formula V.

The 1-phenyl-1,2-dihydro-3H-indazol-3-one compounds of general formula VI are known, or they can be prepared by methods which are known per se (see, for example, Synthesis, 1978, 633–648).

Compounds of formula V are known, or they can be prepared by methods which are known per se, for example by reacting an amine of formula X $$H_2N-R_5 \qquad \qquad X$$

where $R_5$ has the above defined meaning, with a corresponding di(haloalkyl)amine under the conditions customary for the alkylation of amines.

If desired, some of the substituents in the phenyl rings or the indazole matrix in the compounds of formula I or in the abovementioned intermediate products can be subsequently introduced or replaced by other substituents in a manner which is known per se. Thus, for example, halogen substituents can be subsequently introduced into the indazole system by known methods. The corresponding halogenated compounds are obtained with halogenating agents, such as chlorine, bromine, N-chlorosuccinimide, N-chloroacetamide and N-bromosuccinimide.

The compounds of formula I and their pharmacologically acceptable acid addition salts are distinguished by interesting pharmacological properties, and in particular display antiallergic actions. The compounds are also well tolerated and have only a low toxicity, and, in particular there is a wide interval between the therapeutically active dose and the toxic dose.

On the basis of their antiallergic actions, the compounds of formula I and their pharmacologically acceptable salts are suitable as antiallergic agents for the treatment of allergic illnesses, such as, for example, bronchial asthma or allergic rhinitis.

The antiallergic properties of the compounds of formula I can be demonstrated in standard pharmacological tests on small animals. For example, the substances have an inhibiting action on the release of endogenic mediators, from mast cells or basophilic leucocytes, which leads to allergic reactions. The doses to be used vary, of course, depending upon the nature of the substance used, upon the mode of administration and upon the condition to be treated. In general, however, satisfactory results are obtained in animal experiments with peroral doses of between 0.05 and 75 mg. per kg. of body weight. Thus, the new compounds have a specific inhibiting action in the PCA test (passive cutaneous anaphylaxis) in rats which is described below.

Description of the test method to determine the inhibition of passive cutaneous anaphylasis (PCA test, see Arch.int.pharmacology 252 (1981) 316–326).

To prepare the IgE-antiovoalbumin serum, used in this test, by the method of Mota (Immunology 7, (1964) 681) and J. Goose (Immunology 16 (1969) 749), male Wistar rats of 200–250 g. body weight were sensitised by subcutaneous injection of 1 mg. of ovoalbumin and 1 ml. of Bordetella pertussis suspension ("Vaxicoq" Merieux $3 \times 10^{10}$ organisms/ml). After 14 days, the animals are exsanguinated and the blood is centrifuged. The antiserum thus obtained is stored at 20° C.

Non-sensitised rats are injected with in each case 0.1 ml. of antiserum into the skin at in each case four different sites on their shaven backs. After 72 hours, a solution of the test compound, or, for comparison, only the solvent, is administered orally, and 10 minutes later 5 mg. of ovoalbumin and 5 mg. of blue dye (Evans blue) in 0.9% strength sodium chloride solution are administered intraperitoneally. After 30 minutes, the animals are sacrificed and the diameters of the blue spots formed at the sites injected with the antiserum are measured. The inhibiting effect of the test substance is determined from the size of the blue spots which occur.

The table which follows shows the results obtained in the test described above. The Example numbers given for the compounds of the formula I relate to the preparation Examples which follow.

| Test substance of the formula I Example No. | P.C.A. Inhibition $ED_{50}$ mg/kg |
| --- | --- |
| 12 | 22 |
| 18 | 25 |
| 17 | 17.9 |
| 19 | 11.5 |
| 15 | 10.6 |
| 20 | 7.5 |
| 21 | 19.2 |
| 49 | 15.5 |
| 32 | 6.6 |

-continued

| Test substance of the formula I Example No. | P.C.A. Inhibition $ED_{50}$ mg/kg |
| --- | --- |
| 26 | 22 |
| 28 | 5.7 |
| 29 | 14 |

Determination of the minimum toxic dose in mice.

No toxic symptoms were to be observed on oral administration of the above substances in doses of up to 300 mg/kg.

As medicines, the compounds of formula I and their pharmacologicaly acceptable salts can be contained in pharmaceutical preparations, such as, for example, tablets, capsules, suppositories or solutions, together with the customary pharmaceutical solid or liquid diluents or carriers and auxiliaries. These pharmaceutical compositions can be prepared by methods which are known per se, using the customary solid excipients, such as, for example, talc, lactose or starch, or liquid diluents, such as, for example, water, fatty oils or liquid paraffins.

The compounds of formula I can be administered in pharmaceutical use forms which contain about 0.5 to 100 mg., preferably 0.5–25 mg., of active substance per individual dose. The dosage to be used will, of course, vary depending on the species to be treated and the individual requirements. Parenteral formulations will in general contain less active substance than products for oral administration.

The Examples which follow are non-limiting Examples intended to illustrate the preparation of the new compounds of formula I and of the new intermediate products in more detail.

The structures of the new compounds were confirmed by spectroscopic investigations, in particular by accurate analysis of the IR and NMR spectra.

The IR spectra of the 1-phenyl-1,2-dihydro-3H-indazol-3-one compounds show the carbonyl absorption band of the 1,2-dihydro-3H-indazol-3-one ring at about 1700 cm$^{-1}$, and are free from C=N bands, which can be observed in 1H-indazole derivatives.

EXAMPLE 1

1-Phenyl-2-[4-(4-(2-methoxyphenyl)-piperazin-1-yl)-butyl]-1,2-dihydro-3H-indazol-3-one.

(A) 1-Phenyl-2-(4-bromobutyl)-1,2-dihydro-3H-indazol-3-one.

A solution of 26 g. of 1-phenyl-1,2-dihydro-3H-indazol-3-one in 270 ml. of absolute ethanol is added to a solution of 3.2 g. of sodium in 100 ml. of absolute ethanol, whilst stirring and with exclusion of moisture. The mixture is warmed to 80° C. for 30 minutes, and, after the mixture has been cooled, 66 ml of 1,4-dibromobutane are added and the mixture is then heated under reflux for 3 hours. The ethanol is then distilled off in vacuo, the residue is taken up in toluene, the toluene solution is washed with dilute sodium hydroxide solution and water, dried over sodium sulphate and filtered and the filtrate is evaporated in vacuo. The residue is heated at 190°–210° C. for 30 minutes and, after being cooled, is taken up in ether. 19.1 g of crystalline substance having a melting point of 102°–106° C. are obtained.

(B) 19.1 g of 1-phenyl-2-(4-bromobutyl)-1,2-dihydro-3H-indazol-3-one in 360 ml of toluene are heated at 100° C. with 11.7 g of N-(2-methoxyphenyl)-piperazine and 9 ml of triethylamine for 72 hours. After the reaction solution has been cooled, it is washed with water and the organic phase is then extracted with hydrochloric acid (20% strength). The acid phase is extracted once with 50 ml of toluene, and sodium hydroxide solution (50% strength) is then added, whilst cooling with ice, until the reaction is alkaline. The base which has separated out is taken up in methylene chloride, the methylene chloride mixture is washed with water, dried over sodium sulphate and filtered and the filtrate is freed from solvent. 24.8 g of crude base are obtained as a residue.

The residue is dissolved in ether, and a saturated solution of HCl gas in ether is added to the solution. The dihydrochloride thereby separates out in the form of crystals. The salt is filtered off and recrystallised from ethanol, with the addition of a little water. 19.3 g of the dihydrochloride semihydrate of the title compound are obtained.

Melting point: 157°–161° C.

The dihydrochloride monohydrate with 0.3 mol of acetone has a melting point of 168°–188° C.

EXAMPLE 2

1-Phenyl-2-{3-[4-(4-trifluoromethylphenyl)-piperazin-1-yl]-propyl}-1,2-dihydro-3H-indazol-3-one (A) 1-Phenyl-2-(3-chloropropyl)-1,2-dihydro-3H-indazol-3-one.

62 ml of 1-bromo-3-chloropropane are added to a solution of the sodium salt of 1-phenyl-1,2-dihydro-3H-indazol-3-one (prepared from 29.6 g of 1-phenyl-1,2-dihydro-3H-indazol-3-one and 3.6 g of sodium in 300 ml of absolute ethanol) and the mixture is heated under reflux for 17 hours. The ethanol is distilled off in vacuo, the residue is taken up in toluene and the toluene mixture is washed with dilute sodium hydroxide solution and water. After the solution has been dried over sodium sulphate, it is evaporated in vacuo. The crude 1-phenyl-2-[3-chloropropyl]-1,2-dihydro-3H-indazol-3-one (40.5 g) which remains as the residue is chromatographed on ten times the amount of silica gel using toluene/methylene chloride/15% strength ethanol.

15.9 g are obtained.

Melting point: 69° C. (ethyl acetate/hexane)

(B) 1-Phenyl-2-[3-(4-formylpiperazin-1-yl)-propyl]-1,2-dihydro-3H-indazol-3-one.

21.4 g of 1-phenyl-2-(3-chloropropyl)-1,2-dihydro-3H-indazol-3-one are heated under reflux with 22.7 g of N-formylpiperazine and 2.1 g of potassium bromide in 170 ml of isopropanol for 18 hours. The isopropanol is then distilled off in vacuo and the residue is taken up in toluene. The toluene phase is extracted with dilute hydrochloric acid and the hydrochloric acid extracts are rendered alkaline with dilute sodium hydroxide solution and extracted with methylene chloride. After the methylene chloride phase has been washed neutral, it is dried over sodium sulphate and evaporated in vacuo.

17.4 g of 1-phenyl-2-[3-(4-formylpiperazin-1-yl)-propyl]-1,2-dihydro-3H-indazol-3-one are obtained.

(C) 1-Phenyl-2-[3-(piperazin-1-yl-propyl]-1,2-dihydro-3H-indazol-3-one.

17.4 g of the N-formylpiperazine derivative obtained as described under 2B are dissolved in 150 ml of a 1:1 mixture of ethanol and 20% strength hydrochloric acid, and the solution is left to stand at room temperature overnight. It is then heated under reflux for another 2 hours, and the ethanol is distilled off in vacuo. Toluene and dilute sodium hydroxide solution are added to the crude title compound, which remains as the residue, and the toluene phase is washed with water, dried over sodium sulphate and evaporated in vacuo.

12.6 g of crystals having a melting point of 100°–102° C. are obtained.

(D) 1-Phenyl-2-{3-[4-(4-trifluoromethylphenyl)-piperazin-1-yl]-propyl}-1,2-dihydro-3H-indazol-3-one.

13.6 g of the piperazine derivative described under 2C in 100 ml of dimethylsulphoxide are heated at 130° C. with 10 g of 4-trifluoromethylphenyl bromide in the presence of 10 g of potassium carbonate for 16 hours. After the reaction mixture has been cooled, water and dilute hydrochloric acid are added and the mixture is extracted with methylene chloride. The hydrochloric acid phase is rendered alkaline with dilute sodium hydroxide solution and extracted with toluene. The toluene extracts are washed neutral with water, dried over sodium sulphate and evaporated in vacuo. 16 g of 1-phenyl-2-{3-[4-(4-trifluoromethylphenyl)-piperazin-1-yl]-propyl}-1,2-dihydro-3H-indazol-3-one are obtained as the base.

The 1-phenyl-2-[(piperazin-1-yl)-alkyl]-1,2-dihydro-3H-indazol-3-one compounds listed in the table which follows can also be prepared from corresponding compounds of the formula II or III by the processes described in Examples 1 and 2.

| Example No. | $R_1$ | $R_2$ | $R_3$ | $R_4$ | Z | $R_5$ | Salt | Melting point °C. |
|---|---|---|---|---|---|---|---|---|
| 3 | H | H | H | H | n-$C_3H_6$ | Phen | Base | oil |
| 4 | H | H | H | H | n-$C_3H_6$ | 2-Cl—Phen | Base | oil |
| 5 | H | H | H | H | n-$C_3H_6$ | 4-$CH_3O$—Phen | Base | oil |
| 6 | H | H | H | H | n-$C_3H_6$ | 3-$CF_3$—Phen | Base | oil |
| 7 | H | H | H | H | n-$C_3H_6$ | 4-Cl—Phen | Base | oil |
| 8 | H | H | H | H | n-$C_3H_6$ | 3-Cl—Phen | Base | oil |
| 9 | H | H | H | H | n-$C_4H_8$ | 3-Cl—Phen | Base | oil |
| 10 | H | H | H | H | n-$C_4H_8$ | 4-$CH_3O$—Phen | Base | oil |
| 11 | H | H | H | H | $C_2H_4$ | 4-$CH_3O$—Phen | Base | oil |
| 12 | H | H | H | H | n-$C_4H_8$ | Phen | HCl | 175–177 |
| 13 | H | H | H | H | n-$C_3H_6$ | 2-$CH_3O$—Phen | HCl | 130–195 |
| 14 | H | H | H | H | n-$C_5H_{10}$ | 4-F—Phen | HCl | 198–200 |
| 15 | H | H | H | H | n-$C_3H_6$ | 4-F—Phen | Base | oil |
| 16 | H | H | H | H | n-$C_4H_8$ | 2-Cl—Phen | HCl | 120–125 |
| 17 | H | H | H | H | n-$C_4H_8$ | 4-F—Phen | HCl | 157–160 |
| 18 | H | H | H | H | n-$C_4H_8$ | 2-Pyr | HCl | 210–212 |
| 19 | H | H | H | H | n-$C_3H_6$ | 2-Pyr | HCl | 185–190 |
| 20 | H | H | H | H | n-$C_4H_8$ | 4-$CH_3$—2-Pyr | HCl | 175–180 |
| 21 | H | H | H | H | n-$C_3H_6$ | 4-$CH_3$—2-Pyr | HCl | 169–170 |
| 22 | H | H | H | H | n-$C_4H_8$ | 2-$CH_3$—Phen | HCl | 195–200 |

-continued

| Example No. | $R_1$ | $R_2$ | $R_3$ | $R_4$ | Z | $R_5$ | Salt | Melting point °C. |
|---|---|---|---|---|---|---|---|---|
| 23 | H | H | H | H | n-$C_4H_8$ | 2-Thien | Base | 110–115 (d) |
| 24 | H | H | H | H | n-$C_4H_8$ | 3-Thien | Base | oil |
| 25 | 6-Cl | H | H | H | n-$C_4H_8$ | 4-$CH_3$—2-Pyr | Base | 110–112 |
| 26 | 6-Cl | H | H | H | n-$C_4H_8$ | 2-$CH_3O$—Phen | 2 HCl | 184–186 |
| 27 | 6-Cl | H | H | H | n-$C_4H_8$ | 4-F—Phen | HCl | 180–185 |
| 28 | 5-$CH_3O$ | H | H | H | n-$C_4H_8$ | 4-$CH_3$—2-Pyr | 2HCl.1$H_2O$ | 180–185 |
| 29 | 5-$CH_3O$ | H | H | H | n-$C_4H_8$ | 2-$CH_3O$—Phen | Base | 85–87 |
| 30 | 5-$CH_3$ | H | H | H | n-$C_3H_6$ | 2-Pyr | Base | 139–140 |
| 31 | H | H | 2,6-di-$CH_3$ | H | n-$C_4H_8$ | Phen | 2HCl.1$H_2O$ | 160–162 |
| 32 | H | H | 3-$CF_3$ | H | n-$C_4H_8$ | 4-$CH_3$—2-Pyr | 3HCl | 150–155 |
| 33 | 5-$CH_3$ | H | 4-Cl | H | n-$C_4H_8$ | 2-$CH_3O$—Phen | 2HCl | 158–160 |
| 34 | 5-$CH_3$ | H | 4-$CH_3O$ | H | n-$C_4H_8$ | 4-F—Phen | Base | oil |
| 35 | H | H | H | H | n-$C_4H_8$ | 3,4-O—$C_2H_4$—O—Phen | Base | oil |
| 36 | H | H | H | H | n-$C_4H_8$ | 3,4-O—$CH_2O$—Phen | Base | oil |
| 37 | H | H | H | H | n-$C_4H_8$ | 4-Pyr | Base | 155–157 |
| 38 | H | H | H | H | n-$C_4H_8$ | 3-Pyr | Base | oil |
| 39 | H | H | H | H | n-$C_4H_8$ | 2,6-di-$CH_3$—Phen | Base | oil |
| 40 | H | H | H | H | n-$C_4H_8$ | 3,4-di-$CH_3$—Phen | Base | oil |
| 41 | H | H | H | H | n-$C_4H_8$ | 4-OH—Phen | Base | oil |
| 42 | H | H | H | H | n-$C_4H_8$ | 4-$CH_3COO$—Phen | Base | oil |
| 43 | H | H | 3-$CF_3$ | H | n-$C_4H_8$ | 4-F—Phen | 2HCl | 138–140 |
| 44 | H | H | H | H | n-$C_4H_8$ | 4-$CH_3O$—5-Pyr | Base | oil |
| 45 | H | H | H | H | n-$C_4H_8$ | 4-Cl—2-Pyr | Base | oil |
| 46 | 6,7-di-$CH_3O$ | H | H | H | n-$C_4H_8$ | 4-$CH_3$—2-Pyr | Base | oil |
| 47 | H | H | 4-$CH_3O$ | H | n-$C_4H_8$ | 4-F-Phen | Base | oil |
| 48 | 5-F | H | H | H | n-$C_4H_8$ | 4-$CH_3$—2-Pyr | Base | oil |
| 49 | H | H | H | H | n-$C_4H_8$ | 5-$CH_3$—2-Pyr | 3 HCl | 175–180 |

Phen = Phenyl
Pyr = Pyridyl
HCl = Hydrochloride
Base = free base
Thien = Thienyl
oil = oily
(d) = decomposition

EXAMPLE I

Tablets having the following composition are prepared:

| | per tablet |
|---|---|
| 1-Phenyl-2-[4-(4-(2-methoxyphenyl-piperazin-1-yl)-butyl]-1,2-dihydro-3H—indazol-3-one | 25 mg |
| corn starch | 60 mg |
| Lactose | 130 mg |
| Gelatine (10% strength solution) | 6 mg |

The active compound, the maize starch and the lactose are made into a paste with 10% strength gelatine solution. The paste is comminuted; the granules are placed on a suitable metal sheet and dried at 45° C.

The dried granules are passed through a comminuting machine and are mixed, in a mixer, with the following ingredients:

| | |
|---|---|
| Talc | 5 mg |
| Magnesium stearate | 5 mg |
| corn starch | 9 mg | and the mixture is then pressed to tablets weighing 240 mg.

We claim:
1. A compound of the formula II

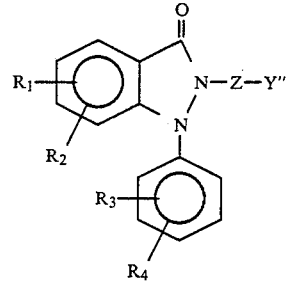

where $R_1$ is a hydrogen or halogen atom, or a lower alkyl, lower alkoxy, or trifluoromethyl radical, $R_2$ is a hydrogen or halogen atom, or a lower alkyl or lower alkoxy radical, $R_3$ is a hydrogen or halogen atom, or a lower alkyl, lower alkoxy or trifluoromethyl radical, $R_4$ is a hydrogen or halogen atom, or a lower alkyl or lower alkoxy radical, Z is an alkylene radical with 2 to 6 carbon atoms and Y" is a halogen atom, or a hydroxyl, lower alkanesulphonyl, benzenesulfonyl or benzenesulphonyl radical which is substituted in the benzene ring by a lower alkyl radical or a halogen atom, or an acid addition salt thereof, with the proviso that Y" is other than chlorine if the substituents $R_1$, $R_2$, $R_3$, and $R_4$ each are hydrogen and Z is an ethylene or propylene group.

2. A compound as claimed in claim 1, wherein at least one of $R_1$, $R_2$, $R_3$ and $R_4$ is other than hydrogen.

3. A compound as claimed in claim 1, wherein Y" is a hydroxyl group.

4. A compound as claimed in claim 1, wherein Y" is a lower alkanesulphonyl group.

5. A compound as claimed in claim 1, wherein Y" is a benzenesulphonyl group or a benzenesulphonyl group which is substituted in the benzene ring by a lower alkyl group or a halogen atom.

6. A compound as claimed in claim 1, wherein $R_1$, $R_2$, $R_3$ and $R_4$ are each hydrogen atoms, Z is a butylene group and Y" is a bromine atom, said compound being 1-phenyl-2-(4-bromobutyl)-1,2-dihydro-3H-indazol-3-one or an acid addition salt thereof.

* * * * *